United States Patent [19]

Rosenberg

[11] Patent Number: 4,690,915

[45] Date of Patent: Sep. 1, 1987

[54] ADOPTIVE IMMUNOTHERAPY AS A TREATMENT MODALITY IN HUMANS

[75] Inventor: Steven A. Rosenberg, Bethesda, Md.

[73] Assignee: The United States of America as represented by the Department of Health and Human Services, Washington, D.C.

[21] Appl. No.: 763,657

[22] Filed: Aug. 8, 1985

[51] Int. Cl.$^4$ .............................. A61K 37/02; 45/05
[52] U.S. Cl. ...................................... 514/2; 514/21; 530/351; 424/101
[58] Field of Search ..................... 424/101; 530/351; 514/2, 21

[56] References Cited

U.S. PATENT DOCUMENTS

| | | | |
|---|---|---|---|
| 4,464,355 | 8/1984 | Fabricius et al. | 514/21 |
| 4,518,584 | 5/1985 | Mark et al. | 424/85 |
| 4,530,787 | 7/1985 | Shaked et al. | 530/351 |
| 4,569,790 | 2/1986 | Koths et al. | 530/351 |
| 4,604,377 | 8/1986 | Fernandes et al. | 514/8 |

OTHER PUBLICATIONS

Cheever et al., *J. Exp. Med.*, 155: pp. 968–980, 1982.
Mule et al., *J. Immunol.*, 1985, 135, 1–7.
Mule et al., *Science*, 1984, 225: 1487–1489.
Rosenberg et al., *Science*, 223: 1412–1415, 1984.
Rosenberg, *Cancer Treatment Reports*, vol. 68, No. 1, 1984.
Shu et al., *Canc. Res.* 1985; 45:1657–1662.

*Primary Examiner*—Johnnie R. Brown
*Assistant Examiner*—Jacqueline M. Stone
*Attorney, Agent, or Firm*—Holman & Stern

[57] ABSTRACT

The present invention discloses a new approach to the therapy of cancer in humans based on the administration of lymphokine activated killer (LAK) cells and interleukin-2 (IL-2). Twelve patients with metastatic cancer who had failed standard available therapy were treated. LAK cells were generated from peripheral blood mononuclear cells obtained at multiple leukaphereses and incubated in the recombinant-derived lymphokine, IL-2. Following three to four days of incubation in IL-2, the resulting LAK cells were capable of lysing fresh tumor cells but not normal cells. These LAK cells were reinfused into the autologous patient, along with the intravenous administration of recombinant IL-2 every 8 hours. Patients received up to 90 doses of IL-2 and from 2.8 to $12.6 \times 10^{10}$ activated cells from up to 14 sequential leukaphereses. Six patients showed objective regression of established cancer.

11 Claims, 12 Drawing Figures

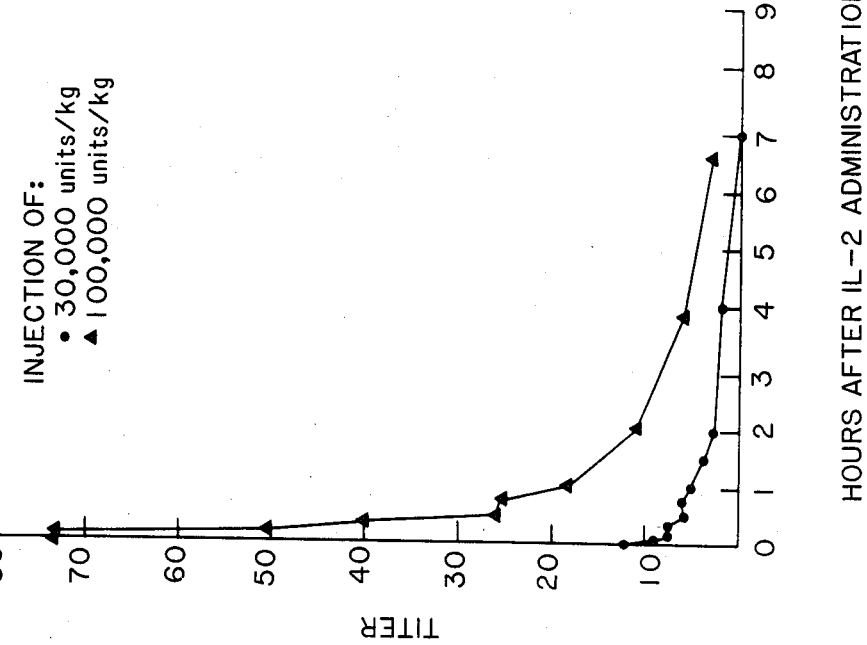
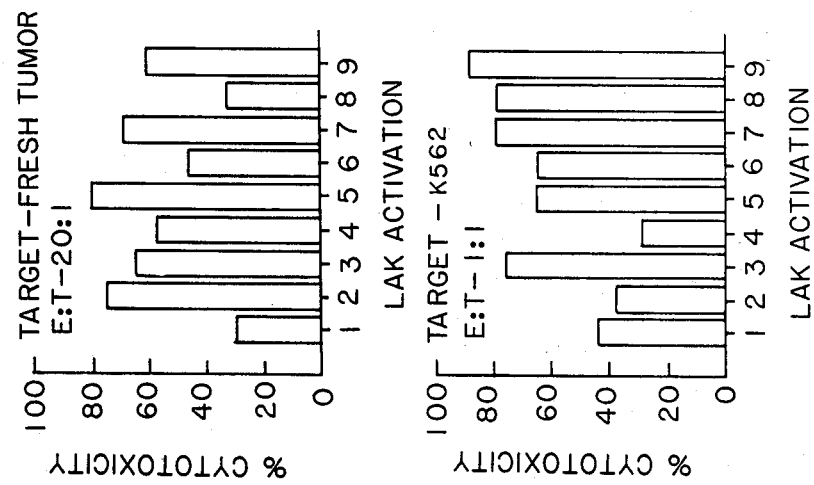

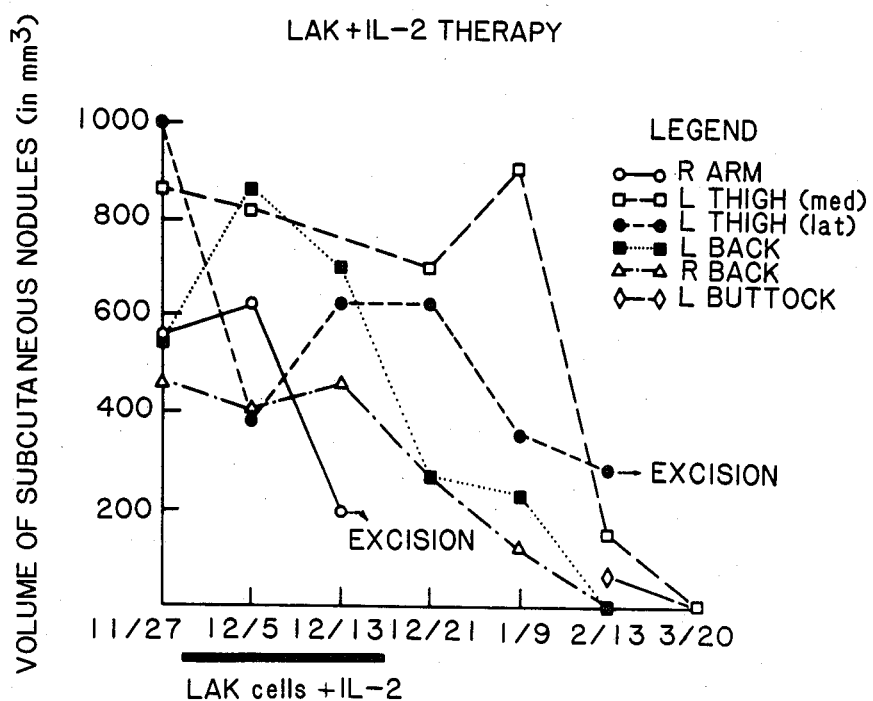
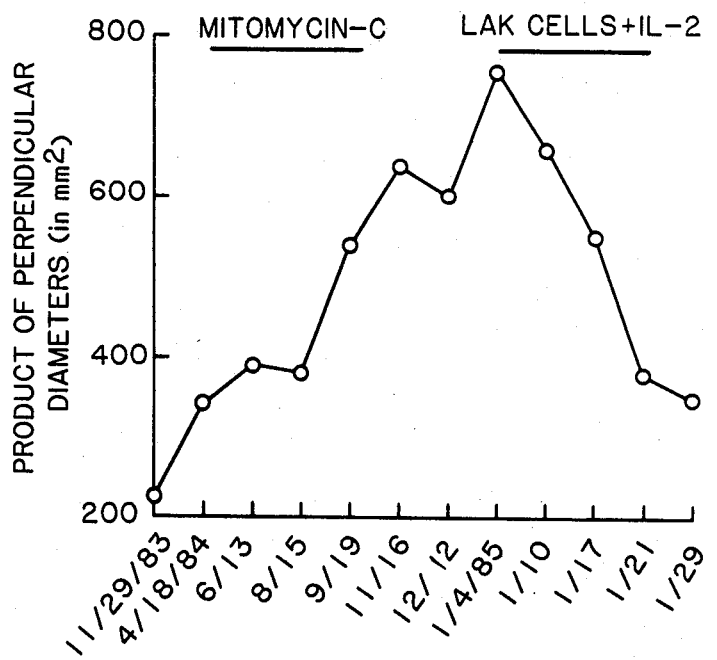

FIG. 6
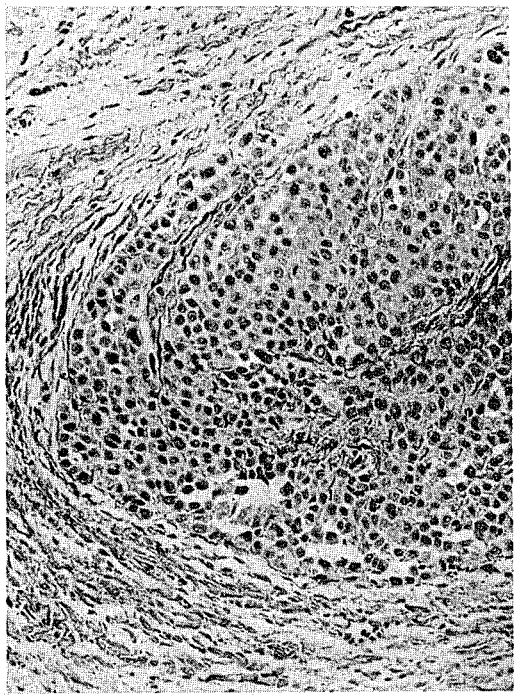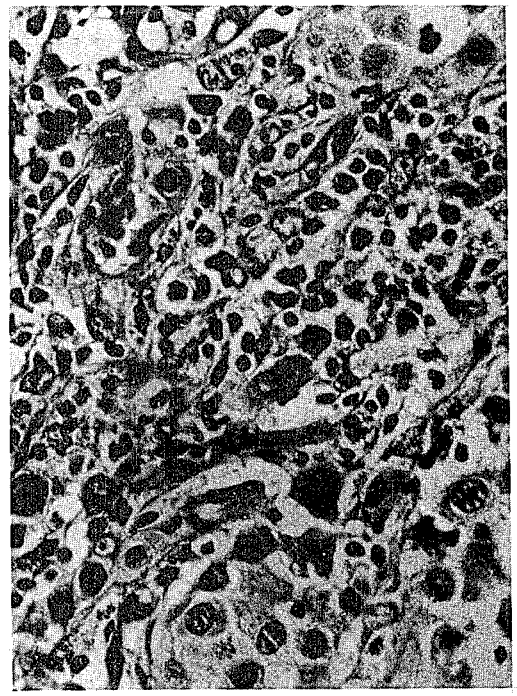

FIG. 8
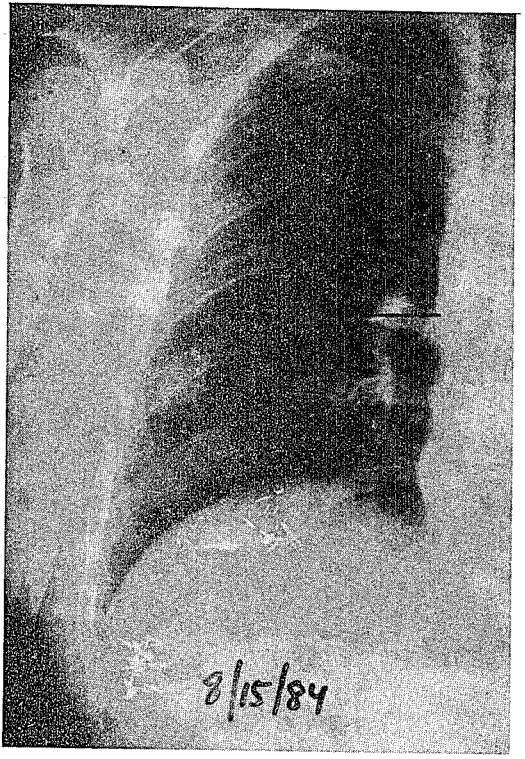
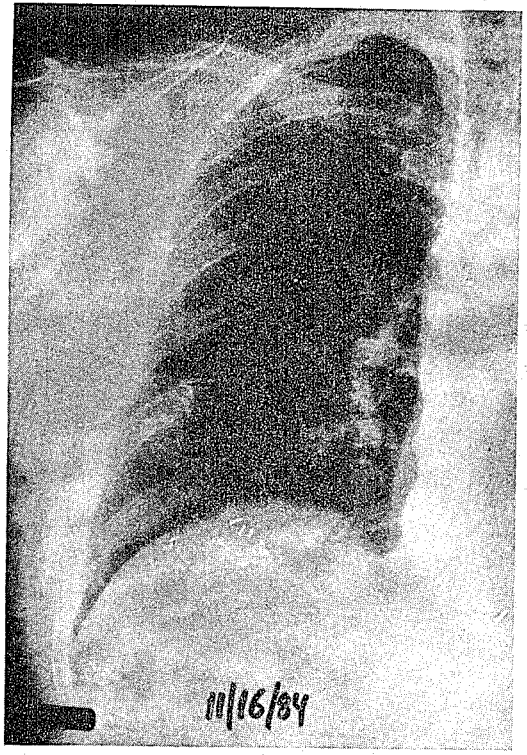
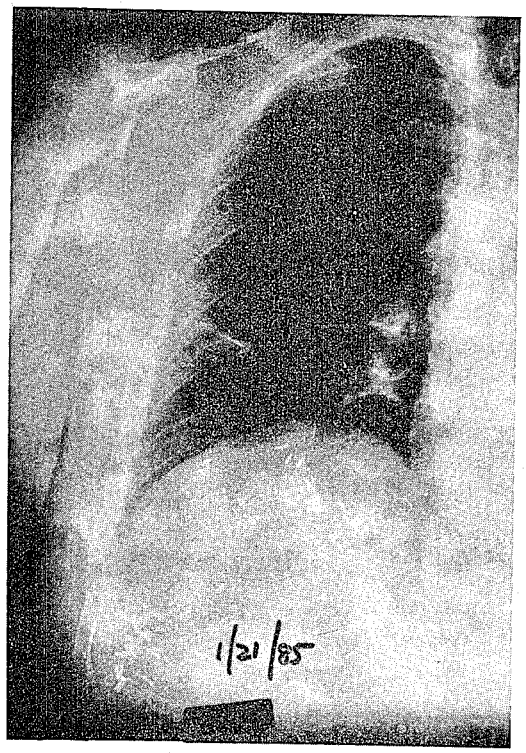

ADOPTIVE IMMUNOTHERAPY AS A TREATMENT MODALITY IN HUMANS

BACKGROUND OF THE INVENTION

1. Technical Field

The present invention is related to adoptive immunotherapy as a treatment modality of certain disease types in humans. More particularly, the present invention is related to a method of treating cancers and other immune dysfunction diseases or conditions in humans using lymphokine activated killer cells in conjunction with the administration of interleukin-2.

2. State of the Art

Attempts have been made during the past two decades to develop immunotherapies for the treatment of cancer based on stimulating the host immune response to the tumor. These approaches were based on attempts to immunize against specific tumor cells or with nonspecific stimulants in the hope that general immune stimulation would concomitantly increase the host antitumor response. Some experimental evidence indicated that this approach might be feasible in the therapy of established tumors. However, the inability to stimulate sufficiently strong responses to putative tumor antigens and the general immunoincompetence of the tumor bearing host, were factors that argued against the success of this approach. In fact initial clinical attempts were unsuccessful and were largely abandoned.

An alternative therapeutic approach to the immunologic treatment of cancer is that of the adoptive transfer of immune cells. Adoptive immunotherapy is defined as the transfer to the tumor-bearing host of active immunologic reagents, such as cells with antitumor reactivity that can mediate, either directly or indirectly, antitumor effects. Adoptive immunotherapy represents an attractive approach to the therapy of cancer and other conditions related to immune-dysfunction. It should be noted that because active immunologic reagents are being transferred to the host, complete host immunocompetence is not required. Thus, the immunosuppression generally associated with the tumor bearing state does not represent a major problem to this therapeutic alternative. Since host immunocompetence is not required, and in fact may be beneficial to the effects of the adoptive transfer of immune cells, adoptive immunotherapy can be easily combined with other therapies such as chemotherapy and radiation therapy. Since the transferred reagents are immunologically specific, this treatment modality predicts a high degree of specificity and consequently a low morbidity. Further, in contrast to most other therapies, no immunosuppression is likely to result from this treatment.

Virtually all prior attempts to perform adoptive immunotherapy have utilized animal models. The feasibility and efficacy of adoptive immunotherapy as a treatment modality for the correction or control of diseases, particularly cancers and immune dysfunction diseases in humans, has not heretofore been demonstrated. A review of previous attempts to perform adoptive immunotherapy of cancer in animals and humans can be found in Rosenberg et al., 1977 Adv. Cancer. Res. 25:323-388.

SUMMARY OF THE INVENTION

It is, therefore, an object of the present invention to provide a method of treating cancer and immune dysfunctions in humans by adoptive immunotherapy.

It is a further object of the present invention to provide human peripheral blood lymphocytes activated with a lymphokine, said activated lymphocytes when administered to humans being selectively capable of destroying tumor cells.

Other objects and advantages of the present invention will become apparent as the detailed description of the present invention proceeds.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 1 shows LAK activity of transferred cells. Peripheral blood mononuclear cells from each leukapheresis on patient No. 2 (listed in Table 2) were activated with IL-2 to generate LAK cells and aliquots were cryopreserved. At the completion of the treatment protocol, all samples were thawed and tested simultaneously for the ability to lyse both fresh NK-resistant tumor cells (upper panel) and the NK-sensitive K562 cell line (lower panel) in a four hour chromium release assay;

FIG. 2 shows serum IL-2 levels following intravenous administration of either 30,000 units/kg or 100,000 units/kg (patient No. 11). A rapid fall in the serum level of IL-2 follows intravenous bolus administration, consistent with a two component half-life of recombinant IL-2 in humans. The first component has a half-life of 6 to 7 minutes and the second, approximately 70 minutes;

FIG. 5 shows time course of the regression of subcutaneous melanoma nodules in patient No. 1. Significant regression of tumor was seen following the completion of LAK cell administration and IL-2. By four weeks after the end of treatment, melanoma nodules were decreasing in size and had disappeared completely by three months after therapy;

FIG. 6 shows sequential biopsies of subcutaneous deposits of metastatic melanoma of patient No. 9. (left) Pretreatment biopsy of a subcutaneous melanoma revealed sheets of melanoma cells with minimal necrosis and only rare lymphoid cells. (right) The biopsy of a metastatic deposit resected two weeks after therapy with LAK cells and IL-2 exhibited a marked chronic inflammatory infiltrate. Individual necrotic tumor cells were seen within the residual viable tumor. (Hematoxylin and eosin; left)×200, (right×500);

FIG. 7 shows the growth of a metastastic colon carcinoma to the lung before and after therapy with LAK cells and IL-2 in patient No. 2. This patient had five pulmonary metastatic lesions. The growth curve of one metastasis is illustrated here. This lesion continued to grow over a two year period and did not respond to treatment with Mitomycin C. Within one week after treatment with LAK cells and IL-2, the lesions began to regress;

FIG. 8 shows pre- and post-treatment X-rays of the lung lesion in the right lung (arrow in upper left panel) illustrated in FIG. 7. The lesion grew progressively prior to initiation of therapy on January 10, 1985. Eleven days later significant regression of the nodule was noted. Two satellite nodules seen just above and to the right of the larger lesion completely regressed (see FIG. 9);

DETAILED DESCRIPTION OF INVENTION

Figure 3:
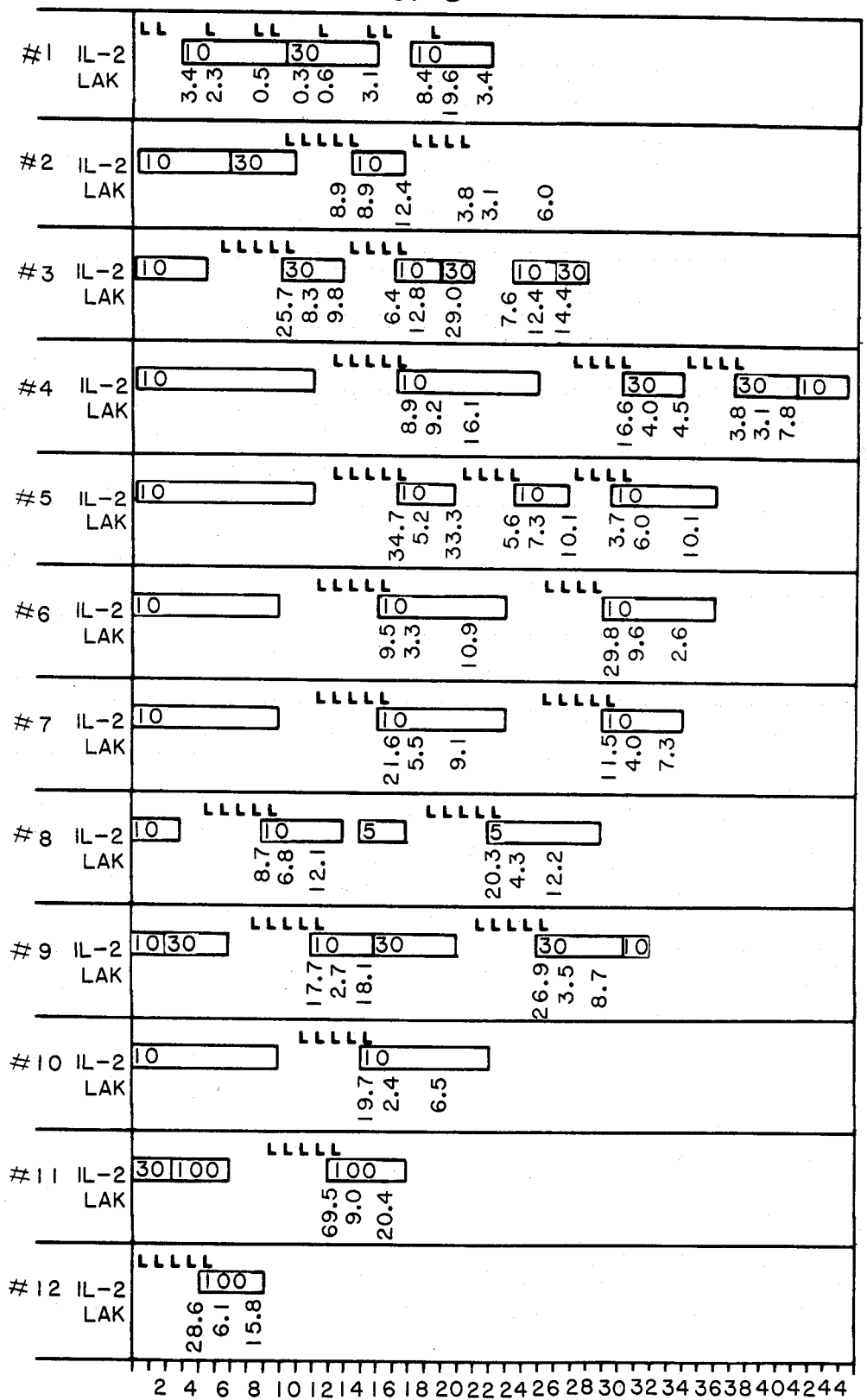
FIG. 3 shows the exact treatment schedule for each of the twelve patients receiving therapy with LAK cells and IL-2. The day of leukapheresis is signified by "L". The days of IL-2 administration are indicated by open boxes. The number inside the box indicates the number of units ($\times 10^{-3}$)/kg administered intravenously every 8 hours. The numbers of LAK cells infused ($\times 10^{-10}$) are also shown. The protocol varied in different patients depending on patient tolerance to therapy and an attempt to administer higher doses of IL-2 as the protocol proceeded.

The above objects and advantages of the present invention are achieved by a composition comprising lymphokine activated human peripheral blood lymphocytes when administered in a suitable pharmaceutically acceptable (sterile and non-toxic) carrier to humans suffering from immune-dysfunction condition or cancer. A preferred lymphokine suitable for activation of said lymphocytes is interleukin-2 (IL-2). IL-2 can be obtained from any suitable source including recombinant IL-2. Such lymphokine actvated cells possessing antitumor activity are herein defined as "lymphokine activated killer (LAK) cells."

Just as LAK cells, so also phytohemagluttinin activated killer cells (PAK cells) can be similarly used. Minimal side effects were observed with LAK or PAK cells.

A major obstacle to the development of successful adoptive immunotherapy has been the availability of appropriate cells for use in adoptive transfer. Preferably, these cells should be available in large numbers; most animal models predict that approximately $10^{11}$ immune cells will be required to treat clinically evident human malignancies. These cells should be immunologically specific for tumor and should be well tolerated when adoptively transferred. The cells should preferably be autologous although this may not be an absolute requirement. Because immunologically active cells tend to be larger than normal resting cells, the "traffic" of these cells is important and administered cells should be able to traffic to sites of tumor in vivo. Further, immune lymphoid cells are capable of proliferating and an ideal cell for adoptive transfer should be capable of expanding in number at the tumor site either by direct antigenic stimulation by tumor or by the presence of additional growth factors. The ability to amplify the effect of the transferred cells can be a major asset in this approach.

Peripheral blood mononuclear cells are obtained at multiple leukaphereses following standard procedures well known in the art and incubated with IL-2. Recombinant IL-2 was preferable because of its easy availability. Following several days of ex vivo incubation in IL-2, usually three to four days, the resulting cells are capable of lysing fresh tumor cells without affecting normal cells. These activated cells are reinfused, preferably by systemic administration, into the autologous patient followed by administration of suitable dosage of recombinant IL-2 at frequent intervals, usually about every 8 hours. Patients received up to 90 doses of IL-2 and from about $2.8\times10^{10}$ to about $12.6\times10^{10}$ activated cells (LAK or PAK) obtained from up to 14 sequential leukaphereses. Depending on the condition of the patient, of course, more or less IL-2 and more or less LAK cells could be administered. The number of lymphocytes may range from $10^6$ to $10^{12}$ cells and the amount of IL-2 may range from $10^3$ to $10^6$ units per kilogram body weight administered multiple times daily.

The activated cells in accordance with the present invention can be employed for the treatment of cancers, viral and other infective diseases, autoimmune diseases, for the correction of immune-deficiency diseases and the like.

It has been found that precursors of LAK cells belong to the subpopulation of "null" lymphocytes that bear neither T nor B cell surface markers. In the human these precursor cells are widely found in peripheral blood, lymph nodes, bone marrow and the thoracic duct.

Although any similar or equivalent methods and materials can be employed in the practice and/or tests of the present invention, preferred embodiments are now described. All publications mentioned hereunder are incorporated herein by reference. Unless defined otherwise, various terms used herein have the same meaning as is well understood in the art to which the invention belongs.

PATIENT POPULATION

Twelve patients with metastatic cancer who had failed standard therapy were treated in this study (Table 1). Five patients had malignant melanoma, three had colorectal cancer, two had sarcomas, one had renal cell cancer and one had an adenocarcinoma of the lung. All patients had clinically evaluable disease either by physical examination or on standard radiographic studies. All patients had undergone actual or attempted surgical excision of their primary disease and had then developed metastases and failed standard therapy, if available. The clinical protocol used to treat these patients was approved by the Clinical Research Committee of the National Cancer Institute as well as by the Food and Drug Administration. Signed informed consent was obtained from all patients prior to entry into the trial.

tinuous flow cell separator (IBM-2997, Cobe Labs, Lakewood, Colo.). Attempts were made to collect about $5 \times 10^9$ to $5 \times 10^{10}$ mononuclear cells per procedure. At a flow rate of about 60–70 ml/min, 10 to 12 liters of whole blood could be processed in approximately 4 hours to achieve this cell yield. Standard acid citrate dextrose (ACD, NIH formula A) was used as the anticoagulant. Vascular access was accomplished by double anticubital venapuncture when possible, although many patients required either single or double lumen central venous catheters. Fifteen milliliters of ACD-A and 3,000 units of heparin (Porcine, preservative free; O'Neil, Jones and Feldman, St. Louis, Mo.) were added to the collection bags at the time of apheresis. The final volume of each leukapheresis pack was 300–400 mls collected in a Fenwal transfer bag (Travenol, Deerfield, Ill.).

TABLE 1

Patients Treated with Lymphokine Activated Killer Cells and Recombinant IL-2

| Patient | Age | Sex | Diagnosis | Evaluable Disease | Prior Treatment |
|---|---|---|---|---|---|
| 1 | 33 | F | Melanoma | Multiple subcutaneous nodules | Wide local excision, lymph node dissection; recurred and treated with monoclonal antibody, no response; treated with interferon, no response |
| 2 | 41 | M | Rectal cancer | Pulmonary metastases | Abdominoperineal resection, radiation therapy, 5-FU; recurred in liver, resected; recurred in lung, resected; recurred in lung again; treated with mitomycin C, no response |
| 3 | 33 | M | Melanoma | Pulmonary, hepatic, bone, lymph node, gallbladder metastases | Wide local excision, lymph node dissection; recurrence treated with monoclonal antibody, no response |
| 4 | 24 | M | Osteosarcoma | Pulmonary metastases | Amputation of lower extremity; adjuvant chemotherapy with doxorubicin; recurred in lung; thoracotomy with biopsy of pulmonary metastases |
| 5 | 42 | F | Melanoma | Pulmonary and subcutaneous metastases | Wide local excision; recurred in lung, resected; recurred in lymph nodes, resected; then recurred in lung again |
| 6 | 36 | F | Synovial cell sarcoma | Pulmonary metastases | Wide local excision, radiation therapy (6600 rads); recurred in lung, resected; recurred in lung two subsequent times resected; then recurred in lung again |
| 7 | 23 | F | Melanoma | Pulmonary, subcutaneous, liver, spleen metastases | Wide local excision, lymph node dissection; recurrence treated with monoclonal antibody, no response |
| 8 | 59 | M | Colon cancer | Hepatic metastases | Sigmoid colectomy; suture line recurrence, re-resection; recurred in liver |
| 9 | 35 | F | Melanoma | Pulmonary and subcutaneous metastases | Wide local excision, lymph node dissection; recurred with subcutaneous metastases, excised; metastasis to femur, irradiated (6,000 rads); recurrence in soft tissues treated with monoclonal antibodies, no response |
| 10 | 54 | F | Colon cancer | Pulmonary metastases | Sigmoid colectomy; recurred with multiple pulmonary nodules; treated with 5-FU and mitomycin C, no response |
| 11 | 54 | F | Renal cell cancer | Pulmonary metastases | Radical nephrectomy; recurred with multiple pulmonary nodules |
| 12 | 40 | F | Lung adenocarcinoma | Primary tumor and pulmonary metastases | Exploratory thoracotomy revealed fixed primary tumor in apex of lung and multiple small pulmonary metastases, biopsied only |

Prior to entering the trial, all patients underwent complete medical evaluation with documentation and measurement of all sites of metastatc disease. Evaluations of tumor response were conducted at the end of therapy and at varying intervals following therapy, generally at two weeks, six weeks, and then every three months thereafter.

Leukapheresis

To obtain large numbers of lymphocytes, patients underwent repeated lymphocytophereses using a con-

Lymphocyte harvest and culture

Mononuclear cells were separated using Ficoll-hypaque density gradients. Two to three parts of Hank's balanced salt solution (HBSS) without calcium and magnesium were mixed with one part of the leukapheresis cell suspension using a plasma transfer set (Fenwal, 4C2240). Forty milliliters of the diluted cell preparation were poured into 50 ml conical centrifuge tubes and were underlaid with 10 ml of lymphocyte separation media (LSM; Litton Bionetics, Rockville, Md.). The gradients were centrifuged at 900×g for 15 minutes, the separated lymphocytes were harvested, washed twice with HBSS and resuspended in LAK activation medium. This medium consisted of RPMI 1640 (low endotoxin; Microbiological Associates, Rockville, Md.), containing 10 units/ml of penicillin, 10 μg/ml of streptomycin sulfate, 2 mM of glutamine, 5 μg/ml of gentamicin sulfate, and 2% heat-inactivated human AB serum (KC Biologicals, Inc., Lenexa, Kans.). One liter of the cell suspension containing about $10^5$ to $10^7$ cells/ml was added to 2.5 liter roller bottles (Corning 25140) and recombinant IL-2 was added at a final concentration of about 1,000 units/ml. Roller bottles were incubated at 378° C. and were continuously rotated at 0.5 to 1 revolution per minute for three to four days. The resulting LAK cells were centrifuged at about 510×g for 15 minutes in 1 liter bottles, the pellets were pooled in 250 ml centrifuge tubes and washed twice more in HBSS without calcium, magnesium or phenol red, and the cells were resuspended in infusion medium consisting of 200 mls of 0.9% sodium chloride containing 5% normal human serum albumin (American Red Cross Blood Services, Washington, D.C.) and 75,000 units of recombinant IL-2. The final cell suspension was filtered through sterile Nytex (110 mesh; Lawshe Instrument Co., Rockville, Md.), and then transferred to a Fenwal transfer pack (Fenwal, 4R2024).

When the harvest process was begun, a 2 ml aliquot was taken from one of the roller bottles and a gram-stain performed to check for the presence of micro-organisms. In addition, an aliquot of the final LAK infusion suspension was cultured for fungi and for aerobic bacteria. An aliquot of the final infused cell suspension was cryopreserved in liquid nitrogen for subsequent immunologic testing.

It may be noted that if necessary, the activated infusible LAK cells can be cryopreserved following standard procedure and these stored cells can be used after thawing at a later time to administer to patients.

Interleukin-2

The recombinant IL-2 used in this trial was obtained from the Cetus Corporation, Emeryville, CA. This IL-2 was produced in *E. coli* transfected with the gene for IL-2 isolated from the Jurkat cell line. The IL-2 was purified to homogeneity and migrated as a single band on SDS polyacrylamide gel electrophoresis. The biologic characteristics of this recombinant IL-2 have been extensively described (Rosenberg, et al., 1984 Science; 223:1412-1415). IL-2 was obtained as a lyophilized powder and was reconstituted with 1.2 ml of sterile water per vial. Each vial contained approximately 0.3 mg of IL-2 (specific activity, 3 to $5 \times 10^6$ units/mg). Less than 0.04 nanograms of endotoxin were present per vial as measured by the limulusamebocyte assay. Each vial also contained 5% mannitol and approximately 130 μg of sodium dodecyl sulfate per mg of IL-2. As mentioned before, IL-2 from non-recombinant sources can, of course, be also used.

Administration of LAK Cells and Recombinant IL-2

LAK cells were administered intravenously through a central venous catheter or into a large peripheral vein in all patients except for patient No. 8 (see Table 1) who received LAK cells by direct infusion into the hepatic artery via a percutaneous catheter. An initial infusion of approximately $10^8$ cells was performed followed five minutes later by the remainder of the cells over approximately 20 minutes. No filters were used in the infusion line. The infusion bag was gently mixed every five minutes during the infusion.

Recombinant IL-2 was diluted in 50 mls of normal saline containing 5% human serum albumin and was infused intravenously over a 15 minute period every 8 hours.

Immunologic Studies

The titer of IL-2 used in these studies was determined by measuring the ability of samples to maintain proliferation of an IL-2 dependent cell line using the procedure of *Rosenberg et al.* 1978, J. Immunol.; 121:1946-1950. The titers used in these experiments were those obtained by the Cetus Corporation and were confirmed. Assays performed on this material along with the international IL-2 standard supplied by the Biologic Response Modifier Program of the Frederick Cancer Research Center, NCI, showed that one unit as used herein corresponded to approximately 0.4 international units.

Aliquots of all infused cells were cryopreserved and at the end of each patient treatment these cells were thawed and tested for LAK activity using standard four hour chromium-release assays against fresh human tumor target cells as described by Lotze et al. 1981, Cancer Res.; 41:4420-4425. In addition, serum and peripheral white blood cells were cryopreserved at regular intervals for immunologic testing.

Administration of LAK Cells and Recombinant IL-2

LAK cells were routinely tested for lysis of fresh natural killer-resistant tumor target cell as well as the natural killer-sensitive K562 cell line. Characteristic results of the LAK assays performed on cells from patient No. 2, are shown in FIG. 1. Maximum LAK cell lysis was seen at effector:target ratios of 20:1 or less, with maximum lysis sometimes seen at effector:target ratios of 5:1. The K562 cell line was consistently more sensitive to LAK lysis than were fresh tumor cell preparations. LAK cell generation was relatively constant throughout the leukaphereses in each treatment cycle.

Patients received bolus injections of IL-2 every 8 hours at doses of either 10,000 units/kg, 30,000 units/kg, or 100,000 units/kg depending on the protocol used in each patient. The characteristic pattern of serum IL-2 levels following IL-2 infusion in patient No. 11 is shown in FIG. 2. Serum IL-2 levels dropped precipitously following the completion of each IL-2 bolus infusion, consistent with the initial 6 to 7 minute half-life of recombinant IL-2 in humans as has been reported by Donohue, 1983, J. Immunol; 130:2203-2208; Chang et al., 1984 J. Biol. Res. Mod.; 3:561-572. Following the administration of 100,000 units/kg serum levels generally fell to 1 to 5 units/ml by the time of the next injection 8 hours later. Lower levels of serum IL-2 were seen when 30,000 units/kg were administered (FIG. 2) and little, if any, IL-2 levels in serum could be measured after administration of 10,000 units/kg. Beause murine tumor models suggested that sustained serum levels of IL-2 were necessary to obtain optimal therapeutic effects, increasing doses of recombinant IL-2 intravenously were utilized as the therapy progressed.

Results of Therapy

The exact treatment schedules used in 12 patients are presented in FIG. 3. Except for patients No. 10, 11 and 12, all patients received at least two cycles of leukapheresis and several patients received three cycles. In all cases an attempt was made to begin the IL-2 infusions at the time of LAK cell administration and to continue IL-2 for at least several days following LAK cell administration, if tolerated by the patient.

Figure 9:
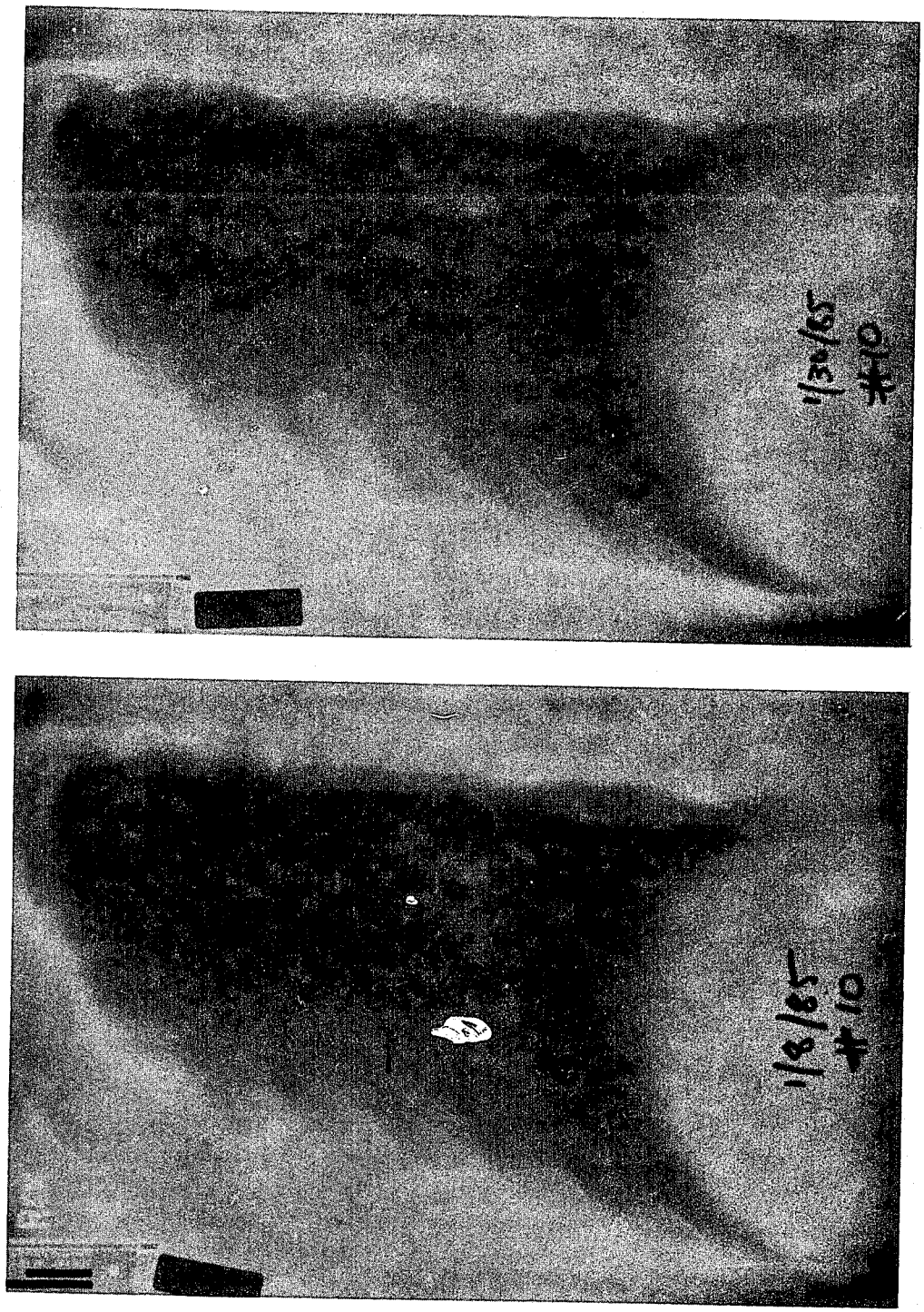
FIG. 9 shows linear tomograms of pulmonary metastases from a patient with colon cancer (patient No. 2). These X-rays illustrate the presence of two metastatic nodules in the right lung (arrow) prior to treatment with LAK cells and IL-2 (left). These two pulmonary metastases completely regressed (right). The configuration of the clips indicates that the same tomographic cut is shown in both X-rays. These metastases have not reappeared after five months of followup.

The doses of LAK cells and recombinant IL-2 in each patient and the results of treatment are presented in Table 2. Six of these 12 patients experienced measurable tumor regression including one complete tumor regression in a patient with metastatic melanoma.

of these latter metastatic lesions is seen in FIG. 7. The pre and post-treatment X-rays of a lesion that partially regressed and of two of the lesions that completely regressed are shown in FIGS. 8 and 9, respectively. The three lesions that disappeared by the end of therapy have not reappeared for the five months following treatment. The two nodules that partially regressed began to grow again after approximately 6 weeks and the patient underwent a second course of therapy with a small diminution in the size of these nodules. The patient is receiving a third course of therapy. Of interest

TABLE 2

Results of Treatment with Lymphokine Activated Killer Cells and Recombinant IL-2

| Patient | Diagnosis | Number of IL-2 doses | Total units IL-2 ($\times 10^{-3}$) | Number of LAK infusions | Total number cells infused ($\times 10^{-10}$) | Result |
|---|---|---|---|---|---|---|
| 1 | Melanoma | 47 | 790 | 9 | 4.2 | Complete regression of subcutaneous metastases |
| 2 | Rectal cancer | 35 | 510 | 9 | 4.3 | Partial regression of pulmonary metastases |
| 3 | Melanoma | 40 | 800 | 13 | 12.6 | No response |
| 4 | Osteosarcoma | 90 | 1340 | 14 | 7.4 | No response |
| 5 | Melanoma | 70 | 700 | 13 | 11.6 | No response |
| 6 | Synovial cell sarcoma | 76 | 760 | 9 | 6.6 | No response |
| 7 | Melanoma | 68 | 680 | 10 | 5.9 | Partial regression of pulmonary metastases |
| 8 | Colon cancer | 42 | 280 | 10 | 6.4 | Partial regression of hepatic metastases |
| 9 | Melanoma | 65 | 1490 | 10 | 7.9 | No response |
| 10 | Colon cancer | 51 | 510 | 5 | 2.9 | No response |
| 11 | Renal cell cancer | 27 | 2280 | 5 | 9.9 | Patial regression of pulmonary metastases |
| 12 | Lung adenocarcinoma | 12 | 1200 | 5 | 5.1 | Partial regression of primary pulmonary tumor |

Figure 4:
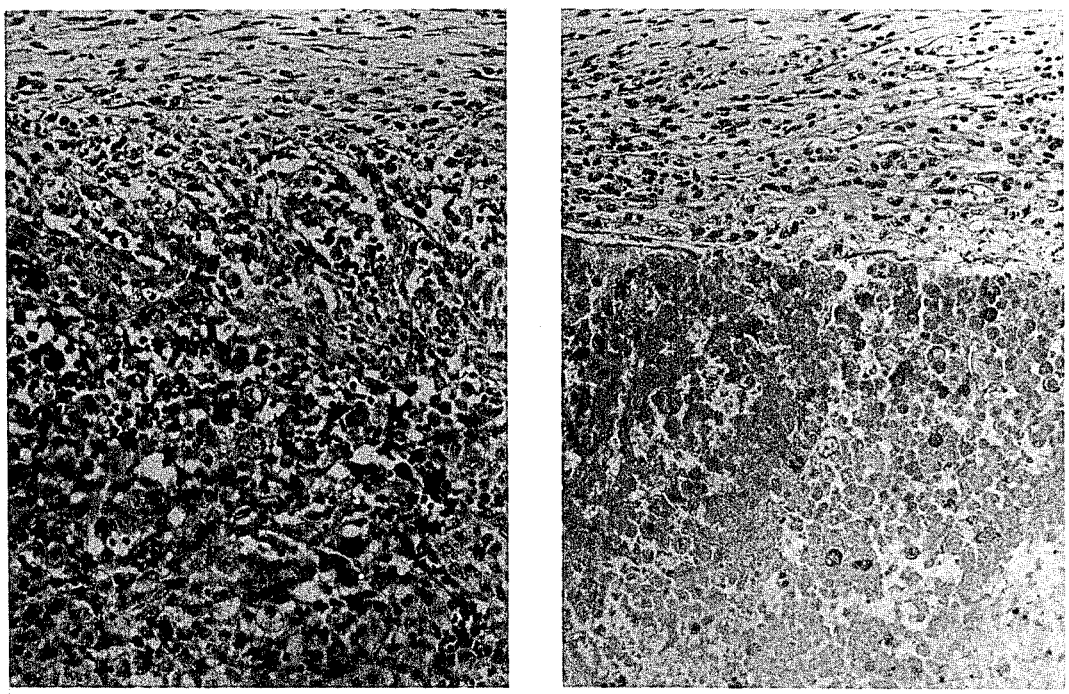
FIG. 4 shows biopsies of subcutaneous metastatic melanoma nodules from patient No. 1. (left) Pretreatment biopsy of a subcutaneous metastasis shows an aggregate of pleomorphic tumor cells with a fibrous pseudocapsule containing a small number of lymphoid cells (right). Biopsy from the same patient taken four weeks after completion of therapy shows extensive coagulative necrosis of the melanoma and increased numbers of chronic inflammatory cells within the fibrous capsule. No viable tumor was seen at this time. (Hematoxylin and eosin; 220)

Patient No. 1 underwent complete regression of all subcuteneous deposits of metastatic melanoma following therapy with LAK cells and IL-2. These lesions stabilized during treatment and, beginning approximately four weeks after completion of therapy, the tumor nodules began to slowly regress. A biopsy taken at 4 weeks after the end of therapy revealed coagulative necrosis of all tumor, chronic inflammation, and fibrosis (FIG. 4). All these lesions regressed completely and this patient has been free of disease for six months following termination of therapy. The time course of the regression of several of these skin lesions with respect to the infusion of LAK cells plus IL-2 is shown in FIG. 5.

Sequential biopsies of the subcutaneous melanomas of another patient (No. 9), excised prior to therapy and at varying intervals after therapy, revealed an extensive infiltration of tumor with "activated" lymphoid cells following LAK cell and IL-2 administration (FIG. 6). Whereas the original tumor exhibited minimal necrosis and contained few lymphocytes, by the end of therapy lymphoid infiltrates were prominent at the tumor margins and scattered among viable and necrotic tumor cells. In this patient, although several nodules exhibited a regression in size other nodules enlarged. This patient (No. 9) was thus considered to have had no clinical response.

Patient No. 2 had rectal cancer with five pulmonary metastases. Three of these metastases disappeared completely as documented by conventional chest X-ray and by linear tomography following therapy with LAK cells and IL-2 and the remaining two metastases, which were somewhat larger, decreased in size but did not disappear. The time course of tumor regression of one are the CEA levels in this patient, which were 159 at the initiation of therapy, 91 after the first course of treatment and 33 after the second course of therapy.

Figure 10:
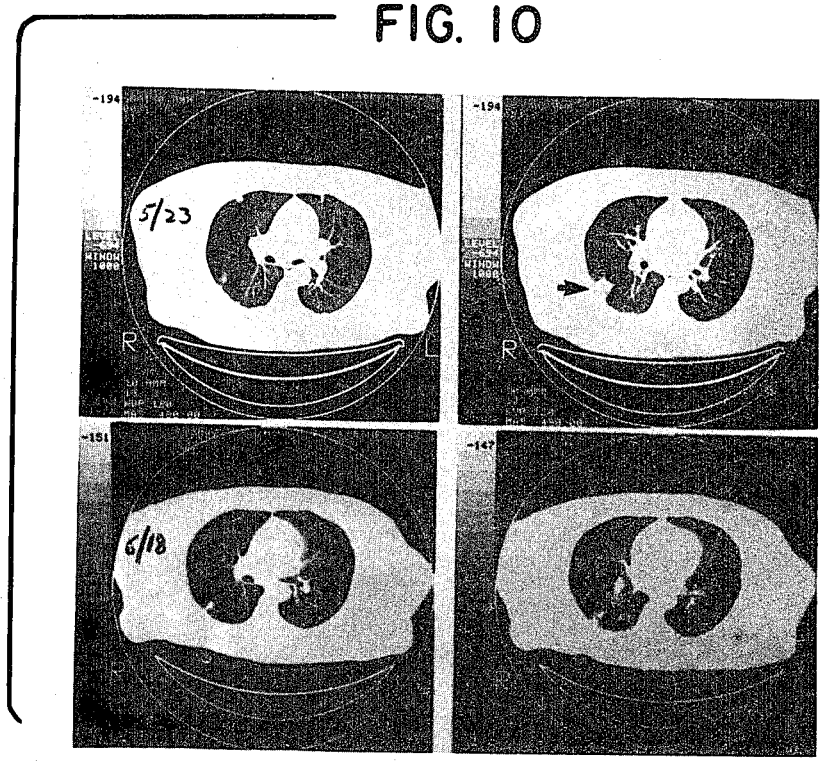
FIG. 10 shows computerized tomograms of the lungs of a patient with metastatic renal cell cancer prior to (upper panels) and after (lower panels) treatment with LAK cells and IL-2 (patient No. 11). Multiple pulmonary nodules were present in this patient (arrow points to one metastasis) all of which regressed significantly within two weeks after completion of therapy with LAK cells and IL-2.
Figure 11:
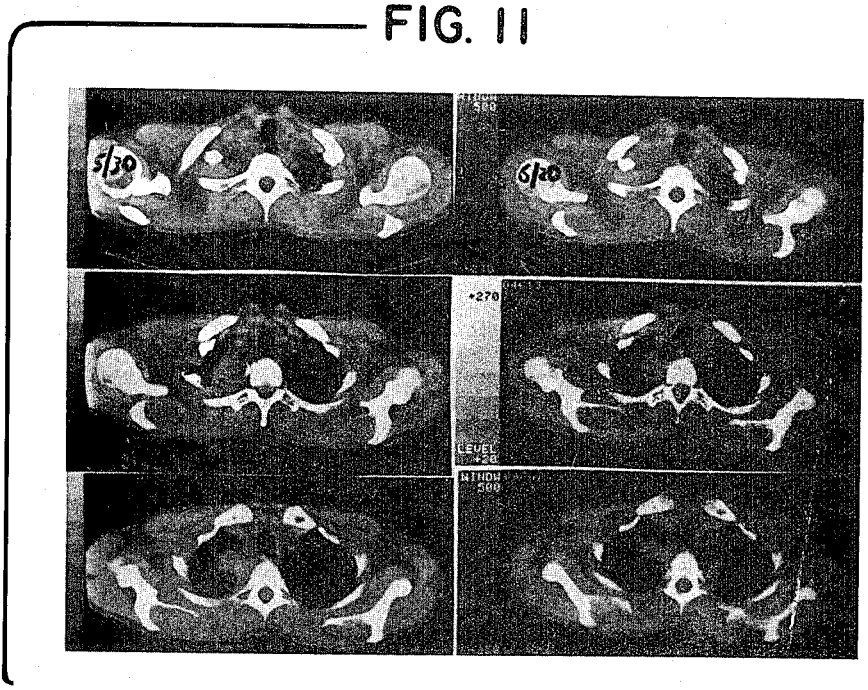
FIG. 11 shows computerized tomograms of the lungs in a patient with an apical adenocarcinoma of the lung (patient No. 12). Sequential CAT scan sections are shown prior to (left) and following (right) treatment with LAK cells and IL-2. Significant regression of this primary apical lung lesion (arrow in left middle panel) was seen within two weeks after completion of therapy.

Patient 8 experienced a partial regression of hepatic metastases from colon cancer as documented by ultrasonography and patient 9 underwent a partial regression of pulmonary metastases from melanoma. These patients had bulky sites of metastatic disease and although a 50% decrease in the volume of lesions was seen, no lesions disappeared completely. Patient No. 11 exhibited a partial regression of pulmonary metastases from a renal cell cancer within two weeks after the completion of therapy (FIG. 10) and patient 12 exhibited a partial response to therapy of a large apical lung adenocarcinoma within two weeks after completion of therapy (FIG. 11). These patients are carefully being followed and will be retreated if less than a complete remission is seen.

Figure 12:
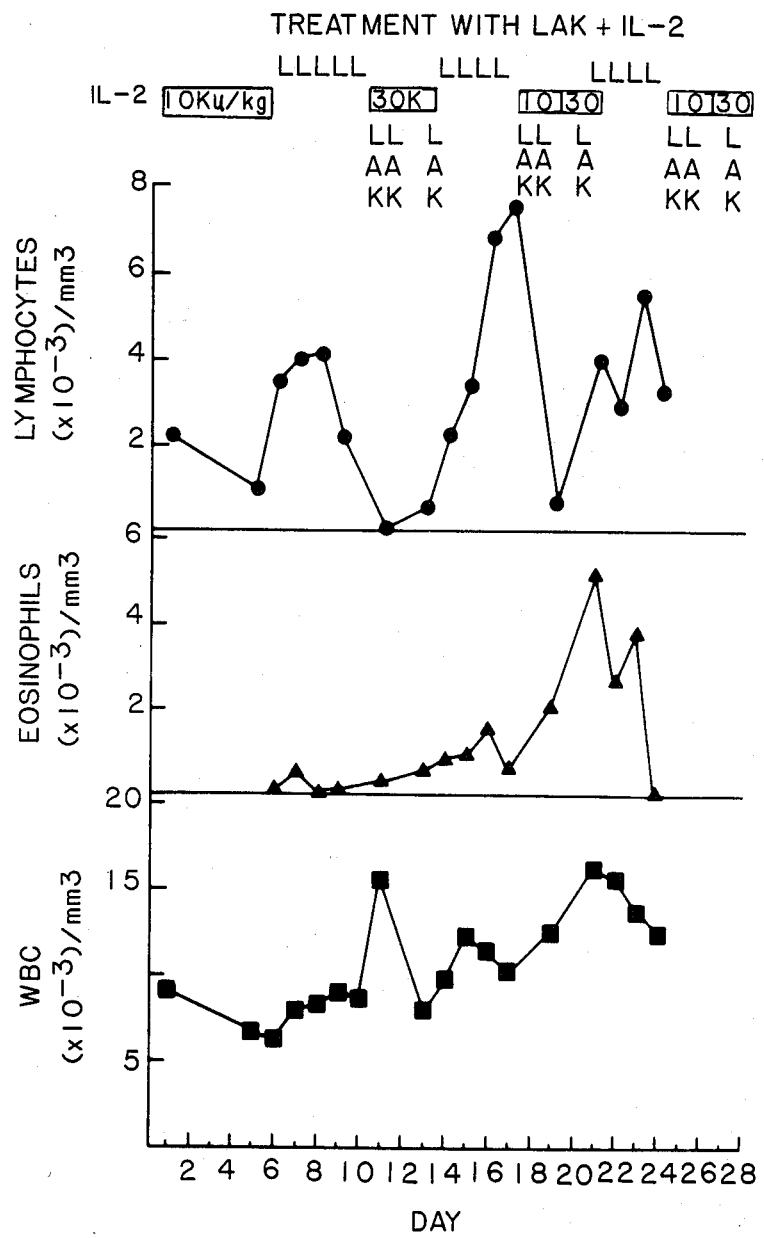
FIG. 12 shows fluctuation in circulating white blood cell counts following administration of LAK cells and IL-2 in patient No. 3. The day of leukapheresis is signified by "L". The dose of IL-2 is shown in the box in units $(\times 10^{-3})$/kg and the day of LAK cell infusion is indicated by "LAK". The number of circulating lymphocytes decreased during IL-2 administration and then exhibited a rebound to above baseline levels within 48 hours after discontinuing IL-2 (top panel). The circulating eosinophils (middle panel) and the total white blood cell count (bottom panel) increased during the course of therapy.

Three major factors were involved in therapy modifications made as the protocol proceeded. These were: (1) There was rapid disappearance of LAK precursors from the peripheral blood during IL-2 administration and thus leukaphereses did not result in acceptable cell yields while IL-2 was being given. Attempts were made to harvest lymphocytes during IL-2 infusion from four pilot patients treated prior to the treatment of the 12 patients reported in this protocol. Minimal numbers of cells were obtained because of the absence of LAK precursors in the circulation during IL-2 administration and none of these four patients received more than $2 \times 10^{10}$ total cells. For this reason leukaphereses were performed after IL-2 administration was discontinued. (2) There was a marked rebound in the number of lymphocytes as well as the number of LAK precursors in the circulation following the discontinuance of IL-2 administration. Therefore, as the protocol proceeded, IL-2 was administered for several days and then IL-2 administration was discontinued approximately 36 hours before beginning leukapheresis. An example of the fluctuation in lymphocyte counts as a function of IL-2 administration in patient No. 3 is shown in FIG. 12. Thus by cycling the administration of IL-2 and leukapheresis, it was possible to markedly increase the number of LAK cells harvested. The toxicity of IL-2 limited the amount of IL-2 that could be given. Animal models indicated that the therapeutic effect was directly related to the number of LAK cells infused and to the amount of IL-2 administered. Because of the toxic side effects associated with IL-2 administration, vide infra, most patients treated in the early phase of this clinical protocol received 10,000 units/kg of IL-2 every 8 hours. Subsequent patients received 30,000 units/kg and patients No. 11 and 12 received 100,000 units/kg. In general, the larger IL-2 doses were not well tolerated for long periods of time, hence fewer treatment cycles were administered.

Toxicity of Treatment

The toxicity of therapy in these patients is presented in Table 3. In previous studies, it was demonstrated that the infusion of activated killer cells alone was accompanied by transient fever and chills and a transient decrease in pulmonary diffusion capacity (Rosenberg. 1984, J. Biol. Resp. Mod.; 3:501-511; Mazumder, et al. 1984, Cancer; 53:896-905). Patients in the current study often had chills immediately following cell infusions which were generally well controlled by the intravenous administration of either meperidine (25 to 50 mg) or morphine (4 to 6 mg).

In this protocol, the major side effect associated with IL-2 administration was weight gain due to fluid retention probably resulting from a generalized increase in capillary permeability. Eight of the 12 patients gained greater than 10% of their starting weight. This fluid retention was most profound in soft tissues resulting in marked peripheral edema but at early times appeared to spare the lungs. Lung water measurements on selected patients given IL-2 at doses of 30,000 and 100,000 units/kg were within normal limits. Late in the course of IL-2 administration, however, fluid retention often resulted in pleural effusions and ascites with radiographic appearance of interstitial edema in the lungs associated with dypsnea in 9 of the 12 patients. Two of these patients (patients No. 1 and 12) developed severe respiratory distress requiring incubation for 1 and 4 days, respectively. In addition, IL-2 infusions were associated with fever and malaise and seven of the 12 patients developed a generalized erythematous rash. The fever, chills and malaise could be eliminated by the use of acetaminophen (650 mg every 6 hours) and indomethicin (25 mg every 6 hours) and many of the patients received these medications. Many patients also received hydroxyzine hydrochloride, an antihistaminic, for treatment of their rash. Sleep medication used in most patients was doxepin. Most patients were maintained on ranitidine (150 mg orally per day) for prophylaxis of gastrointestinal bleeding. Significant renal dysfunction resulting in low urine output was an uncommon side effect and only three of 12 patients developed serum creatinine levels greater than 2 mg/%. Five of 12 patients developed transient hyperbilirubinema of greater than 2 mg/%. Eosinophilia was common and 11 of the 12 patients developed circulating eosinophils which were greater than 5% of the total white cell count and in several patients greater than 80% of the total circulating white cells were eosinophils at the height of IL-2 administration. IL-2 administration also

TABLE 3

| Toxicity of Therapy with LAK Cells and IL-2 | | | | | | | | | | | | | |
|---|---|---|---|---|---|---|---|---|---|---|---|---|---|
| Patient | 1 | 2 | 3 | 4 | 5 | 6 | 7 | 8 | 9 | 10 | 11 | 12 | Total (of 12 patients) |
| Weight gain (>10%) | + | + | − | + | + | + | − | − | + | + | + | − | 8 |
| Fever (days T max >38° C.) | 6/22 | 6/25 | 8/27 | 3/45 | 2/36 | 3/35 | 3/36 | 0/28 | 15/35 | 1/34 | 0/26 | 5/18 | 10 |
| Chills | + | + | + | − | + | + | + | + | + | + | − | + | 10 |
| Nausea and vomiting | + | + | + | + | + | + | + | + | + | + | + | − | 11 |
| Diarrhea | + | + | + | + | + | − | − | − | + | + | + | − | 8 |
| Dyspnea | + | + | − | − | + | + | + | − | + | + | + | + | 9 |
| Erythema or rash | + | + | − | + | + | + | − | − | + | − | + | − | 7 |
| Pruritis | − | − | − | + | + | + | + | − | + | + | + | − | 7 |
| Nasal congestion | + | − | + | + | + | + | + | − | + | + | − | − | 8 |
| Glossitis | + | − | − | − | − | + | + | − | + | + | + | − | 6 |
| Malaise | + | + | + | + | + | + | + | + | + | + | + | + | 12 |
| Renal dysfunction (creat. >2 mg %) | − | + | − | + | − | − | − | − | − | − | + | − | 3 |
| Hyperbilirubinemia (>2 mg/%) | − | − | − | + | − | + | − | − | − | + | + | + | 5 |
| Eosinophilia (highest %) | 8 | 43 | 32 | 85 | 82 | 84 | 55 | 77 | 46 | 20 | 27 | 4 | 11 |
| RBC transfusions (units) | 3 | 7 | 3 | 4 | 5 | 2 | 7 | 6 | 10 | 4 | 9 | 4 | 12 |
| Thrombocytopenia (<50,000/mm³) | − | + | − | − | − | − | − | − | + | − | + | + | 4 | appeared to be associated with hematopoietic suppression. All patients required blood transfusions during the course of therapy to correct anemia and four of 12 patients developed thrombocytopenia with less than 50,000 platelets/mm$^3$.

In all patients adverse effects disappeared promptly after ceasing IL-2 administration and all 12 patients were eventually discharged home for followup. Diuresis generally began within 24 hours after IL-2 was discontinued and could be hastened by the use of diuretics. Other side effects generally disappeared within four to five days after stopping the IL-2. One additional patient, not considered in this report, developed chest pains during the first cycle of cell infusions and therapy was discontinued prior to the completion of one cycle. Subsequent studies did not confirm a diagnosis of myocardial ischemia. This patient was discharged home and was not retreated.

The present study is the first report of the use of lymphokine activated killer (LAK) cells in conjunction with interleukin-2 (IL-2) in the therapy of patients with cancer. This clinical trial was preceded by the demonstration that the administration of syngeneic LAK cells and recombinant IL-2 was capable of mediating the regression of established pulmonary and hepatic metastases in a variety of transplantable murine tumors including immunogenic and non-immunogenic sarcomas, a melanotic and an amelanotic melanoma, a murine colon adenocarcinoma, and a murine bladder cancer in two different strains of mice (Mule, et al. 1984, Science; 225:1487-1489; Mule et al. 1985, J. Immunol.; 135:646-652). In addition, 26 cancer patients were treated with activated killer cells alone (Rosenberg. 1984, J. Biol. Resp. Med.; 3:501-511; Mazumder, et al. 1984 Cancer; 53:896-905) and 39 cancer patients with IL-2 alone (Lotze et al. 1985 J. Immunol.; 134:157-166) prior to combining these therapies in humans. Of the 12 patients treated in this protocol, 6 experienced objective remissions of their metastatic cancer. All patients had advanced metastatic cancer and had previously failed standard therapy, including surgery, chemotherapy and radiation therapy. In addition, some patients had also failed to respond to investigational therapy with monoclonal antibodies or interferon.

In vitro studies have demonstrated that LAK cells are capable of lysing a wide variety of tumor targets in the human but do not lyse normal cells. In a study of 41 consecutive single cell suspensions of human tumors, 36 were significantly lysed by LAK cells including adenocarcinomas of the stomach, ovary, pancreas and colon as well as a variety of sarcomas and melanomas (Rayner, et al. 1985 Cancer; 55:1327-1333). Though little is known about the antigen recognized by LAK cells, without being bound to any specific theory, it is postulated that it is ubiquitously distributed on transformed but not on fresh normal cells. The precursor of the LAK cell in both the mouse and the human appears to be a non-T, non-B "null" lymphocyte. In the mouse, the LAK precursor cells are Thy-1-, Ia- and in the human the precursor cells are Leu-1-, OKT-3-, Leu-7-, OKM-1-. These LAK cell precursors, therefore, are different from natural killer cells both in cell surface phenotype and in their lytic specificity (Grimm et al. 1982 J. Exp. Med.; 155:1823-1841). Natural killer cells lyse cultured target cells and have little, if any, effect on fresh tumor targets. The LAK effector cell, in distinction to the precursor cell, however, appears to be a T cell since in the mouse it bears the Thy-1 antigen. The LAK precursor cell thus appears to be a primitive cell in the T cell lineage which can differentiate into a T cell under the influence of IL-2. The physiologic function of these LAK cells in normal humans is unknown although these cells make good candidates for a role in natural immunosurveillance against transformed cells.

The murine models predicted that both LAK cells plus recombinant IL-2 would be necessary to mediate antitumor effects (Mule et al. 1984 Science; 225:1487-1489; Mule et al. 1985. J. Immunol.; 135:646-652). Although extremely high doses of IL-2 can mediate antitumor effects in the mouse (Rosenberg et al. 1985. J. Exp. Med.; 161:1169-1188) it is not possible to achieve these doses of IL-2 in humans because of the toxicity associated with IL-2 administration. Thus, in the mouse, administration of LAK cells alone or low doses of recombinant IL-2 alone had no antitumor effects. This was corroborated in previous human studies in which twenty-six humans received LAK cells alone, and 39 humans rceived IL-2 alone (16 received the natural human IL-2 and 23 received recombinant IL-2). No antitumor effects were seen (Rosenberg. 1984. J. Biol. Resp. Med. 3:501-511; Mazumder et al. 1984. Cancer; 53:896-905; Lotze et al. 1985. J. Immunol.; 134:157-166). Because the mouse models predicted that a continuous exposure to IL-2 was necessary in vivo, a dose scheme in humans was selected which included every 8 hour intravenous injections. Earlier studies with the continuous infusion of IL-2 showed that even at maximum tolerated doses barely detectable levels of IL-2 could be found in the circulation. When bolus doses were given every 8 hours, however, high serum levels were seen for several hours (FIG. 2).

As described herein, significant antitumor effects were seen in patients when both LAK cells and IL-2 were given concurrently. The six objective responses reported here occurred in four different histologic types of tumors including melanoma, colorectal cancer, renal cell cancer and lung adenocarcinoma. Because of the broad lytic specificity of LAK cells in vitro, it is clear that this treatment modality has applicability to a large number of histologic subtypes of cancer. Five of the six patients achieved objective partial remissions (at least 50% reduction in the volume of tumor) and one patient achieved a complete remission of disease and has been free of tumor for six months following treatment of a disseminated melanoma:. In patient No. 2 who underwent complete regression of three of five pulmonary metastases, the three metastases that disapeared have also not returned whereas the two metastases that only partially regressed began to regrow after approximately one month. These results indicate that elimination of tumor deposits can result in long-term tumor control but that partial tumor elimination may be followed by prompt regrowth of tumor. In murine models extensive search was made for the presence of tumor cells that are resistant to LAK lysis and it could not be demonstrated that such cells exist. In mouse tumor models, metastases that survive LAK and IL-2 therapy are as susceptible to LAK cell lysis, both in vitro and in vivo, as was the original tumor.

Other approaches to improving this therapy have been suggested by the murine models. Minimal tumor burdens are more susceptible to curative LAK therapy than is bulk disease and the utilization of this therapy as an adjuvant treatment immediately following surgery is indicated. Because therapy with LAK cells and IL-2 is not dependent on host immunocompetence (Mule et al.

1985. J. Immunol.; 135:646–652) the present treatment modality may be ideal for combination with chemotherapy and radiation therapy. In addition, the murine experiments indicate that allogeneic LAK cells are as therapeutically effective as syngeneic cells (Mule et al. 1985. J. Immunol; 135:646–652) and that direct organ infusion of LAK cells may be more effective than systemic administration of LAK cells. It should be further noted that the present invention is not limited to LAK cells only. Of course, any other suitable immune cells could just as well be employed. In addition, these LAK or other immune cells having similar properties could also be expanded in tissue culture and then utilized in accordance with the present invention. Furthermore, monoclonal antibodies could also be used to direct both the LAK cells and IL-2 to the tumor cite. Such modifications as mentioned above are not restrictive, of course, and various other modifications will be readily apparent and suggested to one of ordinary skill in the art.

The administration of LAK cells in conjunction with IL-2 as described herein represents a new approach to the treatment of cancer with potential applicability to a wide variety of tumors or immune sensitive conditions. A major advantage of this approach is its broad antitumor specificity. The similarity of results obtained in humans compared to the murine models, reinforces the utility of the adoptive immunotherapy as an efficacious treatment modality for the control of cancer and other immune-related dysfunctions or diseases.

It is understood that the examples and embodiments described herein are for illustrative purposes only and that various modifications or changes in light thereof will be suggested to persons skilled in the art and are to be included within the spirit and purview of this application and the scope of the appended claims.

I claim:

1. A method of treating cancer in humans comprising systemically administering to a human suffering from cancer other than sarcomas, an effective amount of interleukin-2 and interleukin-2-activated autologous human lymphocytes to cause regression of said cancer.

2. The method of claim 1 wherein said cancer is melanoma, lung adenocarcinoma, renal cell cancer, colon cancer, or rectal cancer.

3. The method of claim 2 wherein the amount of interleukin-2 is in the range of about 1,000 to $10^6$ units per kilogram body weight administered multiple times daily as tolerated by the human being treated.

4. The method of claim 2 wherein the amount of the lymphocytes is in the range of about $10^6$ to $10^{12}$ cells.

5. The method of claim 2 wherein said cancer is melanoma.

6. The method of claim 2 wherein said cancer is osteosarcoma lung adenocarcinoma.

7. The method of claim 2 wherein said cancer is renal cell cancer.

8. The method of claim 2 wherein said cancer is colon cancer.

9. The method of claim 2 wherein said cancer is rectal cancer.

10. A method of treating cancer in humans comprising intraveneously administering to a human suffering from cancer other than sarcomas about $10^6$ to $10^{12}$ interleukin-2-activated human lymphocytes and about $10^3$ to $10^6$ units, per kilogram body weight, of interleukin-2 multiple times as tolerated by said human.

11. The method of claim 10 wherein said cancer is melanoma, lung adenocarcinoma, renal cell cancer, colon cancer, or rectal cancer.

* * * * *